US010335217B2

(12) United States Patent
Lindner

(10) Patent No.: US 10,335,217 B2
(45) Date of Patent: Jul. 2, 2019

(54) PEDICLE SCREW WITH LARGE-DIAMETER BONE THREAD

(71) Applicant: Aesculap AG, Tuttlingen (DE)

(72) Inventor: Stephan Lindner, Wurmlingen (DE)

(73) Assignee: Aesculap AG (DE)

(*) Notice: Subject to any disclaimer, the term of this patent is extended or adjusted under 35 U.S.C. 154(b) by 0 days.

(21) Appl. No.: 16/099,241

(22) PCT Filed: May 10, 2017

(86) PCT No.: PCT/EP2017/061232
§ 371 (c)(1),
(2) Date: Nov. 6, 2018

(87) PCT Pub. No.: WO2017/194633
PCT Pub. Date: Nov. 16, 2017

(65) Prior Publication Data
US 2019/0133660 A1 May 9, 2019

(30) Foreign Application Priority Data
May 13, 2016 (DE) .................. 10 2016 108 972

(51) Int. Cl.
*A61B 17/70* (2006.01)
*A61B 17/86* (2006.01)

(52) U.S. Cl.
CPC ...... *A61B 17/8685* (2013.01); *A61B 17/7032* (2013.01); *A61B 17/8625* (2013.01); *A61B 17/7037* (2013.01)

(58) Field of Classification Search
CPC ............ A61B 17/8685; A61B 17/7032; A61B 17/8625; A61B 17/7037; A61C 8/0018; A61C 8/0025

(Continued)

(56) References Cited

U.S. PATENT DOCUMENTS 5,259,398 A * 11/1993 Vrespa ................. A61B 17/863
128/898
8,162,990 B2 * 4/2012 Potash ............... A61B 17/7032
606/266

(Continued)

FOREIGN PATENT DOCUMENTS

DE 102004027881 A1 12/2005
DE 202011107822 U1 3/2012

(Continued)

OTHER PUBLICATIONS

German Search Report for German Application No. 10 2016 108 972.9, dated Jan. 12, 2017, with English translation—11 pages.

(Continued)

*Primary Examiner* — Pedro Philogene
*Assistant Examiner* — David C Comstock
(74) *Attorney, Agent, or Firm* — RatnerPrestia

(57) ABSTRACT

A pedicle screw system includes a receiving sleeve for a longitudinal support, a bone screw and a shank head element. The bone screw has a bone thread configured as an outer thread and a connection thread configured as an inner thread. The shank head element has at the proximal end a head on which the receiving sleeve is mounted and, at the distal end, a connection thread configured as an outer thread screwed into the connection thread of the bone screw. The connection threads are configured as multi-threads, each with a distal connection thread portion and a proximal connection thread portion. The distal connection thread portion and the proximal connection thread portion have an identical thread pitch. The distal connection thread portion has a smaller diameter than the proximal connection thread portion.

11 Claims, 1 Drawing Sheet

Figure 1:
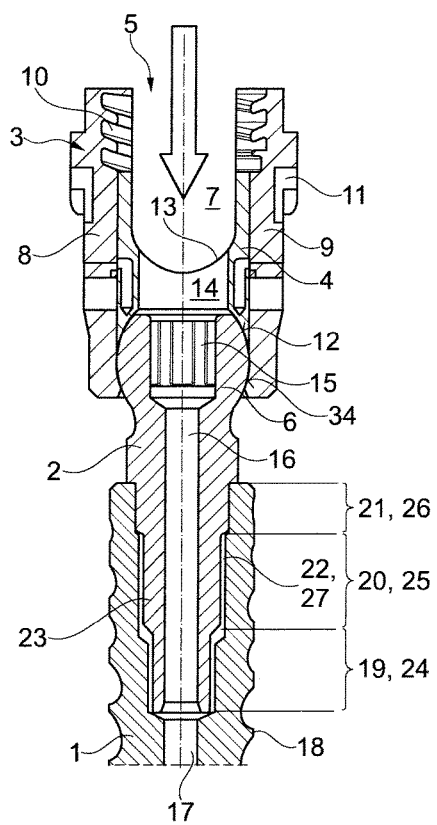

(58) Field of Classification Search
USPC ............ 606/267, 271, 275, 315, 316; 403/7
See application file for complete search history.

(56) References Cited

U.S. PATENT DOCUMENTS

| | | |
|---|---|---|
| 2005/0273101 A1 | 12/2005 | Schumacher |
| 2008/0015596 A1 | 1/2008 | Whipple |
| 2012/0215263 A1* | 8/2012 | Lee .................... A61B 17/7037 606/305 |

FOREIGN PATENT DOCUMENTS

| | | |
|---|---|---|
| GB | 2512063 A | 9/2014 |
| WO | 2014147367 A1 | 9/2014 |

OTHER PUBLICATIONS

International Search Report and Written Opinion for International Application No. PCT/EP2017/061232, dated Aug. 9, 2017—9 pages.

* cited by examiner

PEDICLE SCREW WITH LARGE-DIAMETER BONE THREAD

RELATED APPLICATIONS

This application is the United States national phase entry of International Application No. PCT/EP2017/061232, filed May 10, 2017, which claims the benefit of priority of German Application No. 10 2016 108 972.9, filed May 13, 2016. The contents of International Application No. PCT/EP2017/061232 and German Application No. 10 2016 108 972.9 are incorporated by reference herein in their entireties.

FIELD

The present invention relates to a pedicle screw system comprising a receiving sleeve for a longitudinal support, a bone screw and a shank head element, with the bone screw having a bone thread configured as an external thread and a connection thread configured as an internal thread, wherein the shank head element at the proximal end (from the surgeon's viewpoint) includes a head on which the receiving sleeve is supported and wherein the shank head element at the distal end (from the surgeon's viewpoint) includes a connection thread configured as an external thread and thus is screwed into the connection thread of the bone screw.

BACKGROUND

Basically, pedicle screws serve for dorsally stabilizing the spinal column in the event of fractures, tumors, inflammations, deformations and instabilities caused by degeneration by means of transpedicular screw connection. In so doing, pedicle screws are placed within the pedicles of respective neighboring vertebrae whereupon an angularly stable connection is established between the respective axially superimposing pedicle screws and an axially extending longitudinal carrier or web. The pedicle screws and the longitudinal supports constitute a vertebral stabilizing system.

For this purpose, a pedicle screw usually has an axially extending outer thread as bone thread to which a receiving sleeve (so-called tulip) is connected on the screw-head side. Said receiving sleeve structurally forms a seat being longitudinally slit/tunneled in U-shape and having an inner thread for receiving a longitudinal support, with each of the two radially opposing longitudinal slits defining a slit gap of predetermined gap width. The longitudinal support can be transversely inserted into the longitudinal slits extending in parallel to each other and can be fixed by means of a locking element, for example in the form of a stud screw, threaded nut or set screw screwed into the internal thread.

In the case of a polyaxial pedicle screw a usually spherical or (semi-) spherical shank head is encompassed to be relatively pivoting by the receiving sleeve/tulip and is simultaneously engaged behind in the transition area between the head and the shank. In this way, after countersinking the outer thread shank in the pedicle canal of a vertebra the receiving sleeve/tulip can be pivoted and/or rotated relative thereto so as to obtain a desired position and alignment substantially independently of the alignment of the shank. Accordingly, the undercut prevents the receiving sleeve/tulip from being removed from the shank head.

In practice, there may be cases in which pedicle screws having a large-diameter bone thread are required. Especially with a polyaxial pedicle screw having a large bone screw diameter it may be a problem that the maximum bone screw diameter possible is determined and limited by the geometry and the dimensions of the receiving sleeve. Due to its structure, however, the bone screw has to be passed through the receiving sleeve from the proximal end to the distal end so that the shank head thereof will be located so as to be supported in the receiving sleeve. This is due to the requirement of an as small head part and, resp., an as small receiving sleeve as possible and the small inner diameter of the receiving sleeve resulting therefrom.

In order to solve the afore-described problem, applicant of the present invention already developed a design for a multipart pedicle screw including a bone screw and a shank head element. The bone screw includes a bone thread in the form of an outer thread and a connection thread in the form of an inner thread. The shank head element in turn at the proximal end has a head for supporting the receiving sleeve and at the distal end has a connection thread in the form of an outer thread. The shank head element and the bone screw are connected to each other via the connection threads. Said two-part design offers the advantage that the shank head element may be designed to be adapted to the dimensions of the receiving sleeve such that it may be passed through the latter from the proximal end to the distal end to the stop at the shank head, while the bone screw may be screwed onto the shank head element pre-mounted in the receiving sleeve from the distal direction without having to the passed through the receiving sleeve and is not restricted as regards its bone screw diameter.

A possible problem of said multipart pedicle screw in certain cases may be the fact that the bone thread has to be very flat and tapered in the area of the screwing of the bone screw and the shank head element, viz. in the area of the connection screwing so as to ensure sufficient stability of the bone screw and to be able to reduce or prevent the probability of a rupture of the bone screw due to the thin wall between the bone thread and the connection thread fostered by the high notch effects thereof. However, there are applications in which it is important that the bone screw has a cylindrical or approximately cylindrical threaded core instead of a tapered threaded core.

SUMMARY

Based on the afore-mentioned state of the art, the object underlying the invention is to provide a pedicle screw system which has a cylindrical or approximately cylindrical threaded core with an equal outer diameter, equal screwing strength, equal unscrewing strength and equal biomechanical fatigue strength. Especially, an as large thread depth of the bone thread as possible is to be provided. A transfer of screwing moments ≥12 Nm and a transfer of unscrewing moments ≥10 Nm are intended to be possible. In the case of failure, especially in the case of rupture of the implant, in revision or inadvertent intra-operative dismounting of the implant, the bone thread part is intended to be unscrewed from the bone without any major problems. Finally, between the bone screw and the shaft head element a tight connection is required to ensure sufficient suitability for cleaning.

According to the present invention, this object is achieved by a pedicle screw system, wherein each/both of the connection threads are configured as a (preferably aligned/unidirectional) multi-thread having each of a distal connection thread portion and a proximal connection thread portion. The distal connection thread portion and the proximal connection thread portion have identical or equal thread pitches. The distal connection thread portion has a smaller diameter, especially a smaller nominal diameter, than the proximal connection thread diameter.

By means of the differently large diameters of the distal connection thread portion (small/little) and of the proximal connection thread portion (large/wide) the following contrary effects are achieved: On the one hand, the small distal connection thread portion reduces the notch effect acting on the bone. This enables the screw to counteract high tensile strength/"pull-out strength". On the other hand, the wide proximal connection thread portion allows for increased moment loading of the screw which permits an increased adjusting moment.

In order to be able to ensure safe stable and permanent connection of the bone screw and the shank head element, a particular length of the connection thread is required. According to the idea underlying the invention, the connection thread between the bone screw and the shank head element of known pedicle screw systems is quasi subdivided into plural thread portions. The thread diameters, especially nominal diameters, thereof are different from each other. Proximal connection thread portions have a larger diameter (nominal diameter) than distal connection thread portions. Hence it can be stated that the diameters of the connection thread portions are decreasing from the proximal end to the distal end. Another effect brought about in this way resides in the fact that the wall thickness of the bone screw varies stepwise in the zone of the connection threads, namely in plural steps smaller as compared to prior art (where at the run-out of the connection thread a relatively great change of cross-section having a corresponding notch effect occurs). In this way, on the one hand the notch effect occurring at the end of the connection thread, especially at the distal thread run-out, can be minimized as compared to prior art. On the other hand, the notch effect is spread to a larger portion of the bone screw in the longitudinal direction, viz. to the entire length of the connection thread, by providing plural connection thread run-outs, viz. at each connection thread portion. In total, the invention helps to substantially reduce the loads acting on and the tensions introduced to the bone screw in the zone of the connection thread as compared to prior art while maintaining the thread length. The pedicle screw system according to the invention therefore can be configured to have a (substantially) cylindrical bone thread core while having an identical outer diameter, an identical screwing strength, identical unscrewing strength and identical biomechanical fatigue strength.

Moreover, for the purpose of clarification it is noted that "identical thread pitch" of the proximal and distal connection thread portions in accordance with the invention means that, as regards the pitch thereof, they do not differ by more than 10% relative to each other so that the deviation (possibly) resulting therefrom is tolerable, i.e. the screw remains adapted to be screwed in with said small deviations.

One embodiment of the invention is characterized in that the connection threads of the bone screw are configured as double-threads. The latter include a first distal connection screw portion and a second proximal connection screw portion. Furthermore, the connection threads of the shank head element are configured as double threads, equally comprising a first distal connection thread portion and a second proximal connection thread portion.

Alternatively, or additionally, the thread diameter and the thread pitch of each connection thread portion may be constant.

It is of particular advantage when the shank head element includes a stop on which a stop surface of the bone screw, especially the proximal end face thereof, abuts when the shank head element and the bone screw are completely screwed to each other via the respective connection threads thereof. The multi-thread employed according to the invention causes, jointly with the stop, the bone screw to be subjected to compressive stress in the entire zone between the distal connection thread and the stop. Said compressive stress ensures higher capacity as regards an absorption of biomechanical forces acting on the bone screw. The shank head element and the bone screw may abut on the stop to be especially sealing with each other so that the connection thread will not get stained and is easy to clean.

One embodiment of the invention is characterized in that the bone screw has a central stepped opening extending in the direction of the longitudinal axis, especially in the form of a blind hole or a through-hole. The opening may include plural portions the number of which corresponds at least to the number of the connection thread portions, the portions having different inner diameters relative to each other. Said central opening facilitates screwing the shank head element into the bone screw. In the case of a through-hole, the latter may be used, for example, to insert bone connection material, e.g. bone cement, through the screw to the bone.

One embodiment of the invention is characterized in that the central opening of the bone screw includes a proximal non-threaded portion and a distal non-threaded portion between which the distal connection thread portion and the proximal connection thread portion are arranged. Said non-threaded portions may advantageously be used as positioning aids and facilitate setting the pedicle screw by an operating surgeon.

According to one embodiment of the invention, the shank head element is provided to include a stepped journal comprising a proximal non-threaded portion and a distal non-threaded portion between which the distal connection thread portion and the proximal thread portion are arranged.

It is of particular advantage when the distal non-threaded portion has a smaller diameter than the distal connection thread portion and the proximal non-threaded portion has a larger diameter than the proximal connection thread portion. This helps to reduce or minimize the notch effect due to the change of cross-sections.

Another embodiment of the invention is characterized in that the bone thread includes a cylindrical or substantially or approximately cylindrical threaded core having a substantially constant core diameter. Said bone thread safeguards tight hold of the bone screw within the bone and uniform load introduction over the entire length of the bone thread into the bone material. Another embodiment of the invention is characterized in that the thread depth of the bone thread is constant in the area of the connection thread.

According to one embodiment, the proximal non-threaded portion may have a torx section receiving portion for receiving a torx wrench so as to enable the bone screw to be revised, if the shank head element has come off the bone screw, or to enable the bone screw to be screwed in or unscrewed directly (not via the shank head element).

In an alternative embodiment, the proximal connection thread portion is offset against the distal connection thread portion within a particular tolerance range in the circumferential direction of the screw. When screwing in the screw, certain warping is resulting herefrom which favors tight fastening/the pull-out force to be applied (just as possible deviations of the thread pitch) of the screw.

Summing up, it is stated that the invention enables a two-part bone screw having two or more thread portions which are (substantially) aligned with each other and which have (substantially) identical thread pitches. The thread diameter may decrease from the front to the rear. It can especially be stated that the invention enables a polyaxial pedicle screw system comprising a multi-part, especially two-part, bone screw in which the bone screw has a substantially cylindrical threaded core section with distinct thread depth while having the same outer diameter as a state-of-the-art bone screw with a tapered bone thread.

BRIEF DESCRIPTION OF THE DRAWING FIGURES

Figure 2:
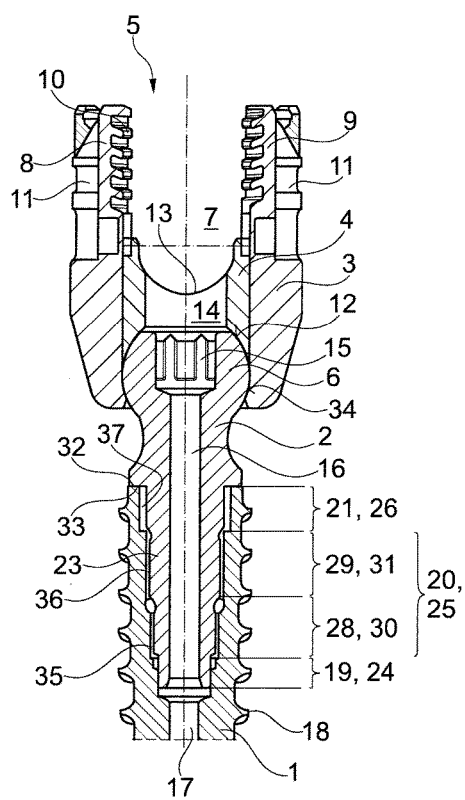

Further features and advantages of the present invention will be evident from the following exemplary and non-limiting description of the invention by way of figures. The figures are merely schematic and only serve for the comprehension of the invention, wherein:

FIG. 1 shows, in a schematic sectional view, a pedicle screw system according to the state of the art, and FIG. 2 shows, in a schematic sectional view, a pedicle screw system according to an embodiment of the invention.

DETAILED DESCRIPTION

Both pedicle screw systems, viz. the one according to prior art shown in FIG. 1 as well as the one according to the invention shown in FIG. 2, comprise a pedicle screw 1, a shank head element 2, a receiving sleeve 4, also referred to as tulip, and a clamping die 4.

The receiving sleeve 3 is a separate component and is movably arranged on the shank head element 2 so that a polyaxial pedicle screw system is formed in which the receiving sleeve 3 can be angularly positioned, especially rotated and/or pivoted, relative to the bone screw 1 and to the shank head element 2. The receiving sleeve has a substantially cylindrical basic form including a through-hole 5 in the longitudinal direction. The distal end zone of the through-hole 5 is formed to be inwardly tapering in the form of a spherical segment in the radial direction and constitutes a ball seat 34 for a ball head 6 of the shank head element 2. At the proximal end, in the receiving sleeve 3 a receiving chamber 7 for a longitudinal support not illustrated in the figures is formed. The latter is laterally accommodated by two radially opposing sleeve wall portions 8, 9 to the inner surfaces of which facing each other an inner thread 10 is introduced. Said inner thread serves for receiving a clamping screw equally not shown in the figures, for example in the form of a conventional stud screw. A tool holder 11 is introduced to each of the outsides of the sleeve wall portions 8, 9 for receiving and coupling a medical instrument for handling the receiving sleeve 3 or the entire pedicle screw system.

In the through-hole 5 the clamping die 4 is disposed. In the radial direction, the latter is adjacent to the sleeve wall surrounding the through-hole 5 and at its distal end includes a semi-spherical receiving surface 12 for a clamping contact with the ball head 6. The proximal end thereof is configured as an approximately shell-type bearing shell 13 for the longitudinal support. It has a central through-hole 14.

The shank head element 2 includes the ball head 6 at its proximal end. A tool holder 15, in this case in the form of a hexagon socket, is introduced to said ball head. The shank head element 2 is also provided with a central through-hole 16 in the direction of the longitudinal axis.

The bone screw 1 equally comprises a central through-hole 17 in the direction of the longitudinal axis. At its radially outer side it is provided with a bone thread 18. The through-hole 17 is widened in the radial direction into the proximal end zone of the bone screw 1.

In the bone screw 1 according to the state of the art a distal widened portion 19, a medial widened portion 20 and a proximal widened portion 21 are formed in the through-hole 17. The medial widened portion 20 is provided with a connection thread 22. The inner diameter of the distal widened portion 19 is smaller than that of the medial widened portion 20 which, in turn, is smaller than that of the proximal widened portion 21. In other words, the inner diameter is increasing from the distal end to the proximal end. The state-of-the-art shank head element 2 has a shank 23 at the distal end. Said shank is stepped, including a distal shank portion 24, a medial shank portion 25 and a proximal shank portion 26. The medial widened shank portion 25 is provided with a connection thread 27. The inner diameter of the distal widened shank portion 24 is smaller than that of the medial widened shank portion 25 which, in turn, is smaller than that of the proximal widened shank portion 26. In other words, the inner diameter is increasing from the distal end to the proximal end. The two connection threads 22, 27 are in threaded engagement and couple the bone screw 1 to the shank head element 2. Due to this design, the shank head element 2 can be inserted from the proximal end to the distal end through the receiving sleeve 3 and then can be screwed with the bone screw 1 so that the latter may be designed to have almost any nominal diameter independently of the geometry of the receiving sleeve 3. It is a drawback of the version shown in FIG. 1 according to the state of the art that the bone screw 1 may rupture at the height of the transition of the medial widened portion 20 to the distal widened portion 21 due to the notch effect occurring there in concentrated form, as due to the bone thread here the wall thickness is very small and thus a large tensile jump is given.

This problem is solved by the invention as shown in FIG. 2. In the bone screw 1 according to the invention, too, in the through-hole 17 a distal widened portion 19 and a proximal widened portion 21 are formed. Between the latter, however, plural, in the present example two, medial widened connection thread portions are formed, viz. a distal connection thread portion 28 and a proximal connection thread portion 29. The inner diameter of the distal widened portion 19 is smaller than that of the distal connection thread portion 28 which, in turn, is smaller than that of the proximal thread portion 29 which, in turn, is smaller than that of the proximal widened portion 21. In other words, the inner diameter is increasing from the distal end to the proximal end.

The shank head element 2 according to the invention has a shank 23 at the distal end. The latter is configured to be stepped with its distal shank portion 24 and its proximal shank portion 26. Therebetween plural, in the present example two, medial widened connection thread shank portions are formed, however, viz. a distal connection thread shank portion 30 and a proximal connection thread shank portion 31. The inner diameter of the distal shank portion 24 is smaller than that of the distal connection thread shank portion 30 which, in turn, is smaller than that of the proximal connection thread shank portion 31 which, in turn, is smaller than that of the proximal shank portion 26. In other words, the inner diameter is increasing from the distal end to the proximal end.

The total of four connection thread portions 28, 29, 30, 31 are in thread engagement, form connection threads 35 and 36, respectively, and couple the bone screw 1 to the shank head element 2. More exactly speaking, the distal connection thread portion 28 is in thread engagement with the distal connection thread shank portion 30 and the proximal connection thread portion 29 is in thread engagement with the proximal connection thread shank portion 31. Due to this design, the shank head element 2 can be inserted from the proximal end to the distal end through the receiving sleeve 3 and then can be screwed to the bone screw 1 so that the latter may be formed with almost any nominal diameter independently of the geometry of the receiving sleeve 3. In the completely screwed state, the bone screw 1 is adjacent, with its end face 32, to a stop 33 formed at the proximal end of the proximal shank portion 26. The double-connection thread 28, 29, 30, 31 causes the entire zone between the distal connection thread 28, 30 and the stop 33 to be subjected to compressive stress. Said compressive stress brings about higher capacity as regards absorption of biomechanical forces possibly acting on the pedicle screw system. Below the proximal connection thread 28, 30 the screw would have, as described before in the state of the art by way of FIG. 1, a preferred failure point and preferably would rupture there. The finer multiple stepping of the diameters according to the invention helps to advantageously reduce and minimize the notch effect.

The bone screw 1 includes at its proximal widened portion 21 a torx section receiving portion 37. Said torx section receiving portion 37 allows for revising the bone screw 1 if the shank head element 2 has separated from the bone screw 1.

The invention claimed is:

1. A pedicle screw system comprising a receiving sleeve for a longitudinal support, a bone screw and a shank head element;
   the bone screw comprising a bone thread formed as an external thread and a connection thread formed as an inner thread;
   the shank head element at a proximal end having a head on which the receiving sleeve is mounted, and the shank head element at a distal end having a connection thread formed as an external thread and screwed into the connection thread of the bone screw;
   the connection threads both being formed as multi-threads, each having a distal connection thread portion and a proximal connection thread portion;
   the distal connection thread portions and the proximal connection thread portions having an identical thread pitch; and
   the distal connection thread portions having a diameter smaller than that of the proximal connection thread portions.

2. The pedicle screw system according to claim 1, wherein the connection thread of the bone screw is formed as a first double thread having a first distal connection thread portion and a second proximal connection thread portion, and the connection thread of the shank head element is formed as a second double thread having a first distal connection thread shank portion and a second proximal connection thread shank portion.

3. The pedicle screw system according to claim 1, wherein the thread diameter and the thread pitch of each connection thread portion are each constant.

4. The pedicle screw system according to claim 1, wherein the shank head element includes a stop on which a stop surface of the bone screw abuts when the shank head element and the bone screw are completely screwed together via their respective connection threads.

5. The pedicle screw system according to claim 1, wherein the bone screw includes a central stepped opening extending in a direction of a longitudinal axis of the bone screw, comprising portions of different inner diameters.

6. The pedicle screw system according to claim 5, wherein the central opening of the bone screw includes a proximal portion being non-threaded or provided with an inner torx section and a distal non-threaded portion, with the distal connection thread portion and the proximal connection thread portion being arranged therebetween.

7. The pedicle screw system according to claim 6, wherein the distal non-threaded portion has a diameter smaller than that of the distal connection thread shank portion and in that the proximal non-threaded portion has a diameter larger than that of the proximal connection thread shank portion.

8. The pedicle screw system according to claim 1, wherein the shank head element has a stepped journal, comprising a proximal non-threaded portion and a distal non-threaded portion, with the distal connection thread shank portion and the proximal connection thread shank portion being arranged therebetween.

9. The pedicle screw system according to claim 1, wherein the shank head element has a central opening extending in a direction of a longitudinal axis.

10. The pedicle screw system according to claim 1, wherein the bone thread includes a cylindrical thread core having a substantially constant core diameter.

11. The pedicle screw system according to claim 1, wherein the thread depth of the bone thread is constant in a region of the connection threads.

* * * * *